US00PP19495P2

(12) United States Plant Patent
Kordes

(10) Patent No.: US PP19,495 P2
(45) Date of Patent: Nov. 25, 2008

(54) SHRUB ROSE PLANT NAMED 'KORFLOCI10'

(50) Latin Name: *Rosa hybrida*
Varietal Denomination: KORfloci10

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/008,684

(22) Filed: Jan. 11, 2008

(51) Int. Cl.
*A01H 5/00* (2006.01)

(52) U.S. Cl. ..... Plt./104
(58) Field of Classification Search ..... Plt./104
See application file for complete search history.

*Primary Examiner*—Annette H Para

(57) ABSTRACT

A new and distinct variety of rose with long lasting, novel light yellow flowers, and attractive foliage with good disease resistance. It exhibits compact growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci10'.

BACKGROUND OF THE INVENTION

The new variety of rose plant of the present invention originated from a controlled crossing in a breeding program of two distinct parents during the summer of 2000. The crossing was between an un-named seedling from the same breeder and 'NOAlesa'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci10'.

SUMMARY OF THE INVENTION

The new rose plant may be distinguished from its seed parent, an un-named seedling, by the following combination of characteristics:

1. The flowers of 'KORfloci10' are light yellow, while the flowers of the seed parent are apricot, and
2. the growth habit of 'KORfloci10' is compact, while the growth habit of the seed parent is vigorous.

The new rose plant may be distinguished from its pollen parent, 'NOAlesa' by the following combination of characteristics:

1. The flowers of 'KORfloci10' are light yellow, while the flowers of the seed parent are yellow,
2. the growth habit of 'KORfloci10' is compact, while the growth habit of the seed parent is upright.

The objective of the hybridization was to create a new and distinct rose plant with unique qualities, such as:

1. Compact and uniform growth and flowering;
2. Abundant attractive, recurrent flowers;

3. Attractive and abundant foliage; and
4. Resistance to diseases encountered in landscapes and gardens.

This combination of qualities is not present in prior rose cultivars. These objectives have been substantially achieved and in that distinguish 'KORfloci10' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci10' was selected in May, 2001 from the seedling beds to be asexually propagated for further evaluation. The first asexual propagation of 'KORfloci10' was done by budding to seedling understocks in July, 2001 at the inventor's nursery in Offenseth-Sparrieshoop, Germany.

This initial and other subsequent propagations conducted in controlled environments demonstrate that 'KORfloci10' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORfloci10'. Specifically illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORfloci10', as observed growing in September, 2007 in a nursery in Jackson County, Oregon on plants of four years of age. Color references are made using The Royal Horticultural Society (London, England) Colour Chart, 2001 except where common terms of color are used.

For a comparison, several physical characteristics of the rose variety 'KORquelda', a rose variety from the same inventor described and illustrated in U.S. Plant Pat. No. 17,048 and issued on Aug. 22, 2006 are compared to 'KORfloci10' in Chart 1.

CHART 1

| Characteristic | 'KORfloci10' | 'KORquelda' |
|---|---|---|
| Petal count | Double (20-25) | Very double (40) |
| Overall height | 70-75 cm | 100-125 cm |
| Flowers per stem | 4-7 blooms per stem | 3-6 blooms per stem |

Parents:

*Seed parent.*—An un-named seedling.

*Pollen parent.*—'NOAlesa'.

Classification:

*Botanical classification.*—*Rosa hybrida*, 'KORfloci10'.

*Commercial classification.*—Shrub rose.

FLOWER AND FLOWER BUD

Blooming habit: Recurrent.

Flower bud:

*Size.*—Upon opening, 32–35 mm in length from base of receptacle to end of bud and 25–27 mm diameter at its widest point.

*Bud form.*—Long and pointed ovoid.

*Bud color.*—As sepals first unfold, bud color on the marginal zone of petal is Yellow Group 8B. Bud color on middle zone of petal is Yellow Group 8C. When ¼ open, the upper surface of petals is Yellow Group 5D, and the lower surface is Yellow Group 4D with intonations of Orange-Red Group 35B.

*Sepals.*—Size: Average 24–28 mm long×8–9 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner side: Pubescent. Covered in fine hairs. Outer surface: Smooth. No hairs observed. Color: Upper surface: Yellow-Green Group 146C with intonations of Greyed-Purple 184C. Lower surface: Yellow-Green Group 144A.

*Receptacle.*—Surface: Smooth. Color: Yellow-Green Group 144A. Shape: Funnel shaped. Size: 5–6 mm (h)×7–8 mm (w).

*Peduncle.*—Surface: Smooth. Length: 18–24 mm average length. Diameter: 1–1½ mm average diameter. Color: Yellow-Green Group 144B.

*Strength.*—Strong.

*Borne.*—Multiple flower buds per stem, generally 4 to 7.

Flower bloom:

*Fragrance.*—Light.

*Duration.*—On the plant 3–6 days. Long lasting. Senesced petals drop away cleanly.

*Size.*—Medium flowered garden rose. When open, the average flower diameter is 65–75 mm and the average flower height is 30 mm.

*Form.*—Shape of flower when viewed from the side: Upon opening, upper part: Flat. Upon opening, lower part: Flattened convex. Open flower, upper part: Flattened convex. Open flower, lower part: Concave.

Color:

*Upon opening, petals.*—Outermost petals: Outer Side: Marginal zone: Yellow Group 4D. Middle zone: Yellow Group 4C. Inner Side: Marginal zone: Yellow Group 4C. Middle zone: Yellow Group 4B. Innermost petals: Outer Side: Yellow Group 4B. Inner Side: Yellow Group 4A.

*Upon opening, basal petal spots.*—Basal petal spot, outermost petals: Outer Side: Yellow Group 4B. Inner Side: Yellow Group 4A. Basal petal spot, innermost petals: Outer Side: Yellow Group 4A. Inner Side: Yellow Group 5A.

*After opening, petals.*—Outermost petals: Outer Side: Yellow Group 2D. Inner Side: Yellow Group 2D. Innermost petals: Outer Side: Yellow Group 2D. Inner Side: Yellow Group 2D.

*After opening, basal petal spots.*—Basal petal spot, outermost petals: Outer Side: Yellow Group 4B. Inner Side: Yellow Group 4A. Basal petal spot, innermost petals: Outer Side: Yellow Group 4B. Inner Side: Yellow Group 4A. Variegations: None.

General tonality: On open flower, Yellow Group 2C. No change in the general tonality at the end of the 5th day. Afterwards, general tonality is Yellow Group 2D.

Petals:

*Petal count.*—Double. Approximately 20–25 petals under normal conditions.

*Petal reflex.*—Petals reflex somewhat.

*Petal edge.*—Slightly ruffled.

*Petal shape.*—Deltoid. Apex shape is round. Shape of base is rounded.

*Petal size.*—30–32 mm long; 35–37 mm wide.

*Thickness.*—Average.

*Petal arrangement.*—Generally in a regular pattern with overlapping edges.

Petaloids: Present.

*Petaloid count.*—Average of 4–6 per flower.

*Petaloid edge.*—Smooth.

*Petaloid texture.*—Smooth.

*Petaloid shape.*—Obovate. Base: acute. Apex: rounded.

*Petaloid size.*—Petaloids are 10–12 mm long and 6–10 mm wide.

*Petaloid color.*—Color of inner side is Yellow Group 4A. Color of outer side is Yellow Group 4B.

Reproductive organs:

*Pistils.*—Approximately 60–70 present. Stigmas: Location: Inferior in position to anthers. Color: Yellow-Green Group 1B. Length: 6–8 mm long. Color: Yellow-Green Group 154D.

*Stamens.*—Abundant. Approximately 120–140 on average and regularly arranged. Anthers: Size: 2 mm long. Color: Margins: Yellow-Orange Group 17A. Middle: Yellow-Green Group 13C. Pollen: Absent. Filaments: Color: Yellow Group 13B. Length: 6–9 mm.

THE PLANT

*Plant growth.*—Moderate vigor. Compact habit. When grown as a budded nursery plant the average plant height is 70–75 cm and the average plant width is 60–65 cm.

*Stems.*—Stem color: Young wood: Yellow-Green Group 144A. Older wood: Yellow-Green Group 146B. Stem surface: Young wood: Smooth. Older wood: Smooth.

*Prickles.*—Present. Incidence: 6–8 per 10 cm of stem. Size: Average length: 9–10 mm. Color: Immature prickles: Base: Greyed-Purple Group 185B. Apex: Greyed-Yellow Group 160A. Mature prickles: Base: Greyed-Yellow Group 161B. Apex: Greyed-Yellow Group 160A. Senescing to Greyed-Orange Group 164C. Shape: Deeply concave to concave. Anthocyanin: Color on base and middle zone of prickle: Greyed-Purple Group 185A. Color on apex of prickle: Greyed-Yellow Group 160A.

*Leaves and leaflets.*—Normally 5–7 leaflets on normal leaves in middle of the stem. Leaf size: 90–100 mm (l)×70–80 mm (w). Quantity: Abundant. Texture: Upper side of leaflet: Glossy and smooth. Under side of leaflet: Matte and smooth. Color, mature foliage: Upper Leaf Surface: Green Group 139A. Lower Leaf Surface: Yellow-Green Group 147B. Color, juvenile foliage: Upper Leaf Surface: Green Group 139A. Lower Leaf Surface: Yellow-Green Group 147B. Anthocyanin intonation: Present. Location: Intonations present on juvenile leaf margins and upper and lower sides of leaf leaf margins and upper and lower sides of leaf surfaces. Color: Greyed-Purple Group 183A.

*Stipules.*—Size: 16–17 mm long. 8–9 mm between the tips of the stipule. Main body of stipule 6–7 mm in width. Shape: Elongated and winged. Stipule color: Margins: Green Group 137B. Center: Yellow-Green Group 144B. Anthocyanin: Slight intonations of Greyed-Purple Group 184B. Presence of stipitate glands: Present on margins. Margins: Serrated. With stipitate glands.

*Petiole.*—Length: 6–10 mm. Diameter: 1–1½ mm. Petiole color: Green Group 137C. Anthocyanin present on juvenile tissue. Color: Greyed-Purple Group 184B. Underneath: A few small prickles underneath. Stipitate glands: Limited numbers of stipitate glands on margins.

*Rachis.*—Length: 12–14 mm. Diameter: 1–1½ mm. Color: Green Group 137C. Anthocyanin present on juvenile tissue, specifically noted on the margins of rachis: Greyed-Purple Group 184B. Margins: With limited numbers of stipitate glands. Yellow-Green Group 154B. Stipitate glands: Limited numbers of stipitate glands on margins.

*Leaflets.*—Size: Average size of the terminal leaflet is 50–55 mm (l)×30–35 mm (w). Shape: Ovate. Base: Ovate. Apex: Acute. Margins: Serrated. Texture: Leathery and glossy.

Hips/seed formation: Observed. Size: 10 mm (l)×15 mm (w). Color: Green Group 143C.

Winter hardiness: To date, the variety has been grown successfully in Zone 5.

Disease resistance: Very good resistance to powdery mildew, rust, Black spot disease under normal growing conditions.

I claim:

1. A new and distinct variety of rose plant characterized by the following combination of characteristics:

(a) Forms attractive, long lasting light yellow flowers;

(b) Exhibits compact growth habit;

(c) Propagates well using traditional methods, and;

(d) Exhibits very good resistance to disease under normal growing conditions, substantially as herein illustrated and described.

* * * * *

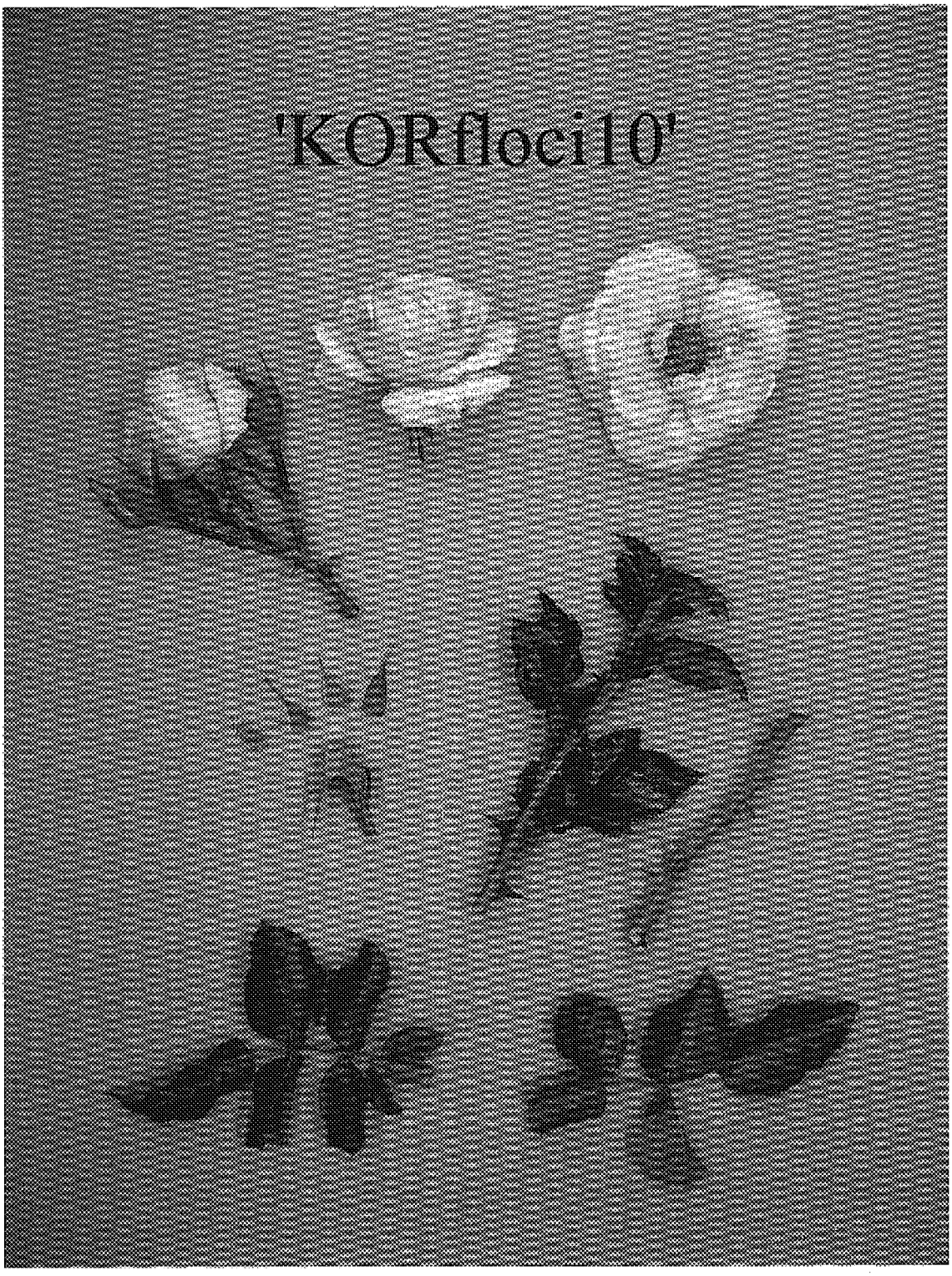
'KORfloci10'